US009176110B1

(12) United States Patent
Kim et al.

(10) Patent No.: US 9,176,110 B1
(45) Date of Patent: Nov. 3, 2015

(54) METHOD OF DETERMINING HISTAMINE CONCENTRATION IN FISH

(71) Applicants: Moon S. Kim, Silver Spring, MD (US); Kuanglin Chao, Ellicott, MD (US); David P. Bannon, Hopkinton, MA (US)

(72) Inventors: Moon S. Kim, Silver Spring, MD (US); Kuanglin Chao, Ellicott, MD (US); David P. Bannon, Hopkinton, MA (US)

(73) Assignees: The United States of America, as represented by the Secretary of Agriculture, Washington, DC (US); Headwall Photonics, Inc., Fitchburg, MA (US)

( * ) Notice: Subject to any disclaimer, the term of this patent is extended or adjusted under 35 U.S.C. 154(b) by 55 days.

(21) Appl. No.: 14/026,684

(22) Filed: Sep. 13, 2013

(51) Int. Cl.
G06K 9/00 (2006.01)
G01N 33/483 (2006.01)

(52) U.S. Cl.
CPC .................. *G01N 33/4833* (2013.01)

(58) Field of Classification Search
CPC .......... G01N 33/12; G01N 2021/3155; G01N 2021/6421; G01N 21/94
See application file for complete search history.

(56) References Cited

U.S. PATENT DOCUMENTS 4,550,085 A * 10/1985 Skov et al. ............. 436/98
6,587,575 B1 * 7/2003 Windham et al. ............. 382/110
7,460,227 B1 * 12/2008 Kim et al. ............. 356/317
7,759,128 B2 * 7/2010 Oguri ............. 436/164
7,787,111 B2 * 8/2010 Kim et al. ............. 356/73
2009/0087033 A1 * 4/2009 Chao et al. ............. 382/110
2010/0096277 A1 * 4/2010 Abu Bakar et al. ......... 205/777.5
2013/0024161 A1 * 1/2013 Cialini et al. ................. 702/186

FOREIGN PATENT DOCUMENTS

WO   WO 9627796 A1 * 9/1996

OTHER PUBLICATIONS

Sun, Da-Wen, ed. Hyperspectral imaging for food quality analysis and control. Chapter 8, Elsevier, 2010.*
Yoshinaga, Derrick H., and Hilmer A. Frank. "Histamine-producing bacteria in decomposing skipjack tuna (Katsuwonus pelamis)." Applied and Environmental Microbiology 44, No. 2 (1982): 447-452.*
Wedge Community Co-op, "Gassing the Tuna—Unnatural Pink Comes to Dinner," Mar. 2005.*
Richard Lawley, "Scombrotoxin (Histamine)," Food Safety Watch, Jan. 30, 2013.*
Don Comis, "Machine's Eye View of Poultry and Produce", Jan. 2007, Agriculture Research, p. 18-19.*

* cited by examiner

*Primary Examiner* — Gandhi Thirugnanam
(74) *Attorney, Agent, or Firm* — Robert D. Jones; John D. Fado; Lesley Shaw

(57) ABSTRACT

A histamine concentration level of a fish item is determined by illuminating the fish and analyzing the resulting spectral image data. Specifically, an algorithm is applied to the fish image data so that a histamine concentration value is calculated for every pixel of the fish image. A corresponding histamine concentration image of the fish is produced based on the collective histamine concentration values. The fish is accepted or rejected based on the collective histamine concentration values and/or the histamine concentration image. The histamine concentration image may be used to identify specific parts of a fish fillet that exceed (or do not exceed) a predetermined histamine concentration level.

19 Claims, 6 Drawing Sheets
(2 of 6 Drawing Sheet(s) Filed in Color)

METHOD OF DETERMINING HISTAMINE CONCENTRATION IN FISH

FIELD OF THE INVENTION

The disclosed method and apparatus relates to a method of determining histamine levels in fish. Specifically, the method described herein relates to a passive multispectral method of inspecting fish fillets and generating an image depicting the histamine concentration of the portion of the fish shown in the image.

BACKGROUND OF THE INVENTION

Histamine fish poisoning is an entirely preventable condition and is among the most common toxicities related to fish ingestion. According to the US Centers for Disease Control and Prevention, approximately 37% of all seafood-related food-borne illnesses result from histamine poisonings.

In harvested fish, histamine is formed by the breakdown of histidine. Histidine exists naturally in many types of fish, and at temperatures above 16° C. (60° F.), histidine is converted to the biogenic amine histamine, via the enzyme histidine decarboxylase. The enzyme histidine decarboxylase is produced by enteric bacteria (including *Morganella morganii*). Histamine is not destroyed by normal cooking temperatures—consequently even properly cooked fish may cause histamine poisoning.

The US Food and Drug Administration established a regulatory threshold of 50 ppm histamine per 100 grams of fish. In most cases, histamine levels in illness-causing fish have been above 200 ppm. Histamine poisoning can cause severe discomfort. Histamine poisoning produces symptoms sometimes mistaken for those of allergic reactions (e.g. rashes, flushes, tingling, itching, etc.). In healthy adults the discomfort rarely lasts longer than one day, however in the young, elderly, or immunocompromised the effects may be more serious.

Members of the Scrombroidae family such as tuna, mahi mahi, and bluefish are most commonly associated with histamine poisoning. Rapid chilling of fish immediately after harvest is the most important element in any strategy for preventing histamine formation.

A number of test kits are currently available to test for the presence and concentrations of histamines. However, these kits require that a technician physically sample and interact with each piece of fish tested. Further, a negative result (i.e. an indication that the fish is safe) is only applicable to the specific sample of meat tested. Current tests do not yield (or guarantee) results for the entire piece of fish.

The need exists for a passive test that provides quick and reliable histamine concentration level information for the entire piece of fish inspected. The method described herein is quick and accurate and provides information regarding the histamine concentration on the entire piece of fish. Further, the current method is much less labor-intensive than prior art methods because it does not require a technician to physically touch any portion of the fish.

SUMMARY OF THE INVENTION

This disclosure is directed to a method of distinguishing wholesome fish from unwholesome fish based on the histamine concentration level of the fish. In accordance with the method, a fish item is illuminated with a light in the visible to near-infrared regions from 400 nm to 1000 nm. A line scan hyperspectral imaging camera system comprising an imaging spectragraph acquires hyperspectral reflectance image data for the fish. Within the hyperspectral reflectance image data, a first light waveband (designated $HC_1$), and a second light waveband (designated $HC_2$) are identified. An algorithm (which includes $HC_1$ and $HC_2$) is applied to distinguish wholesome fish from unwholesome fish.

BRIEF DESCRIPTION OF THE DRAWINGS

The USPTO patent or patent application file associated with this disclosure contains at least one drawing executed in color. Copies of this patent or patent application publication with color drawing(s) will be provided by the Office upon request and payment of the necessary fee.

DETAILED DESCRIPTION OF PREFERRED EMBODIMENTS

The method described herein comprises a multispectral method of determining the histamine concentration in a selected fish item. The apparatus components associated with the current method are well known in the art. The apparatus is generally described in U.S. Pat. No. 7,787,111 to Kim et al., which is hereby incorporated by reference.

Although the term "fish" is used generically herein, a fish is any member of a paraphyletic group of organisms that consist of all gill-bearing aquatic craniate animals that lack limbs with digits. For the purposes of this disclosure, an inspected "fish" or "fish item" (used interchangeably) may comprise a whole or partial processed or unprocessed fish or any portion of a fish or a fish-based item. The term "fish" may also include any composite item which may comprise flesh/material from a fish.

Figure 1:
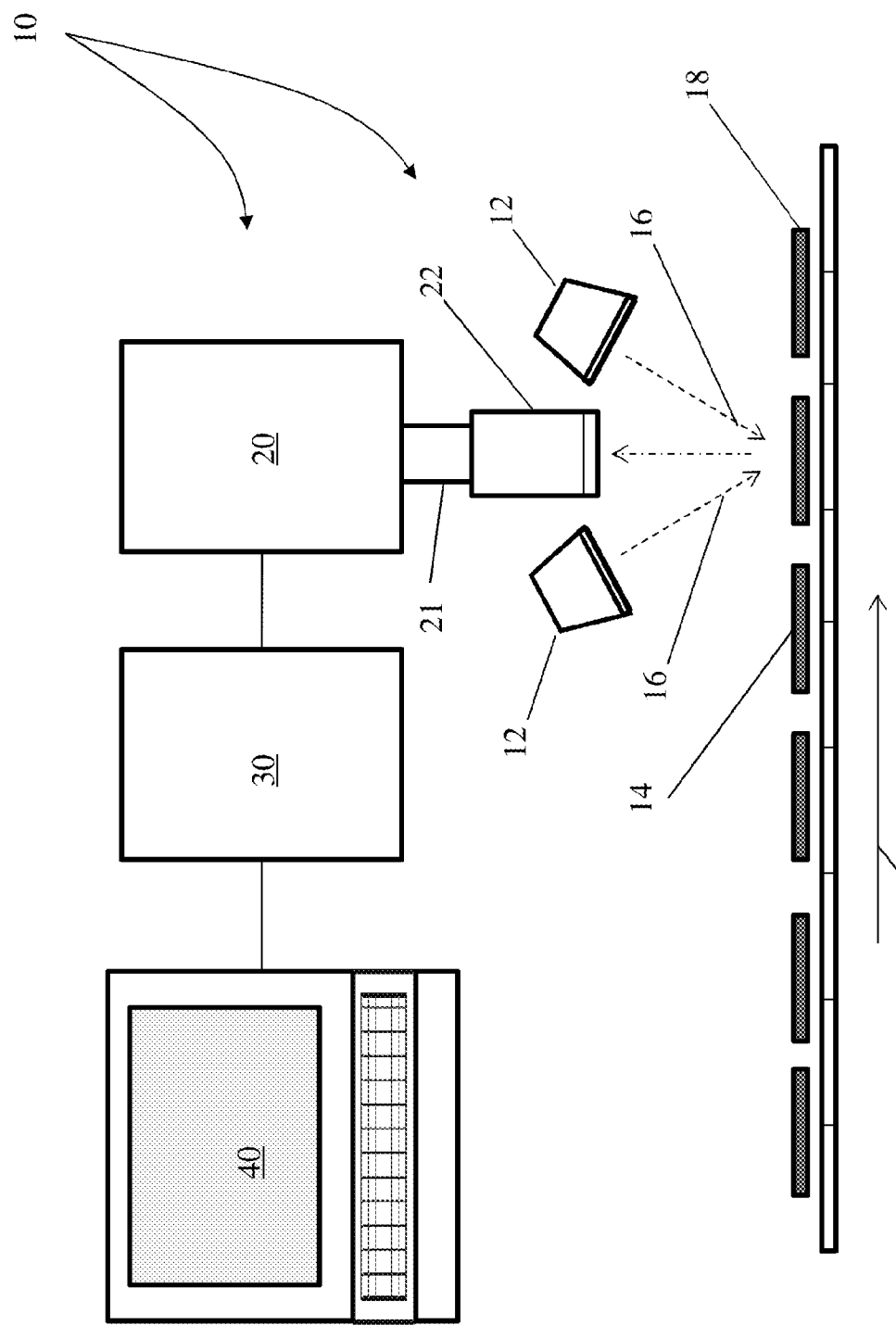
FIG. 1 is a schematic of the apparatus associated with the method described herein.

As generally shown in FIG. 1, the apparatus 10 comprises at least one light 12 which illuminates a generally planar fish fillet 14 with a spectrum of light directed in the direction of the arrows 16. In the preferred embodiment, the spectrum of light includes at least 400 nm-1000 nm, and the inspected fish fillet 14 is positioned on a conveyor 18 moving in the direction of the arrow 19. Although FIG. 1 shows the fish 14 on a conveyor 18, the fish may be positioned under the lights 12 in any manner known in the art, and the lights may be positioned in alternative configurations.

Hyperspectral reflectance image data from the illuminated fish fillet 14 is received and processed by a line scan digital camera 20. The camera 20 includes a lens 22 and an imaging spectrograph 21, or other spectral filtering components configured so that specifically selected light wavebands are received and processed by the camera 20 and processor 30. The processor 30 utilizes an algorithm to determine a concentration of the histamine indicated by the image data. The processor 30 communicates data to a computer station 40 where a processed image may be displayed and/or manipulated.

Specifically, in accordance with the algorithm, two key wavebands in the image data are selected for investigation. A reflected intensity value associated with each of the two key wavebands is determined. The concentration of histamines for the selected fish fillet 14 is determined by a ratio of the reflectance intensity value of the first waveband ($HC_1$) to the reflectance intensity value of the second waveband ($HC_2$). In the preferred embodiment, the $HC_1$ is 610 nm±10 nm, and $HC_2$ is 635 nm±10 nm.

In alternative embodiments, the width of the key wavebands $HC_1$ and $HC_2$ may be modified according to the needs of an operator. A wider or narrower key waveband range may be advantageous, and key wavelengths other than 610 nm and 635 nm may be used in some circumstances.

Figure 3:
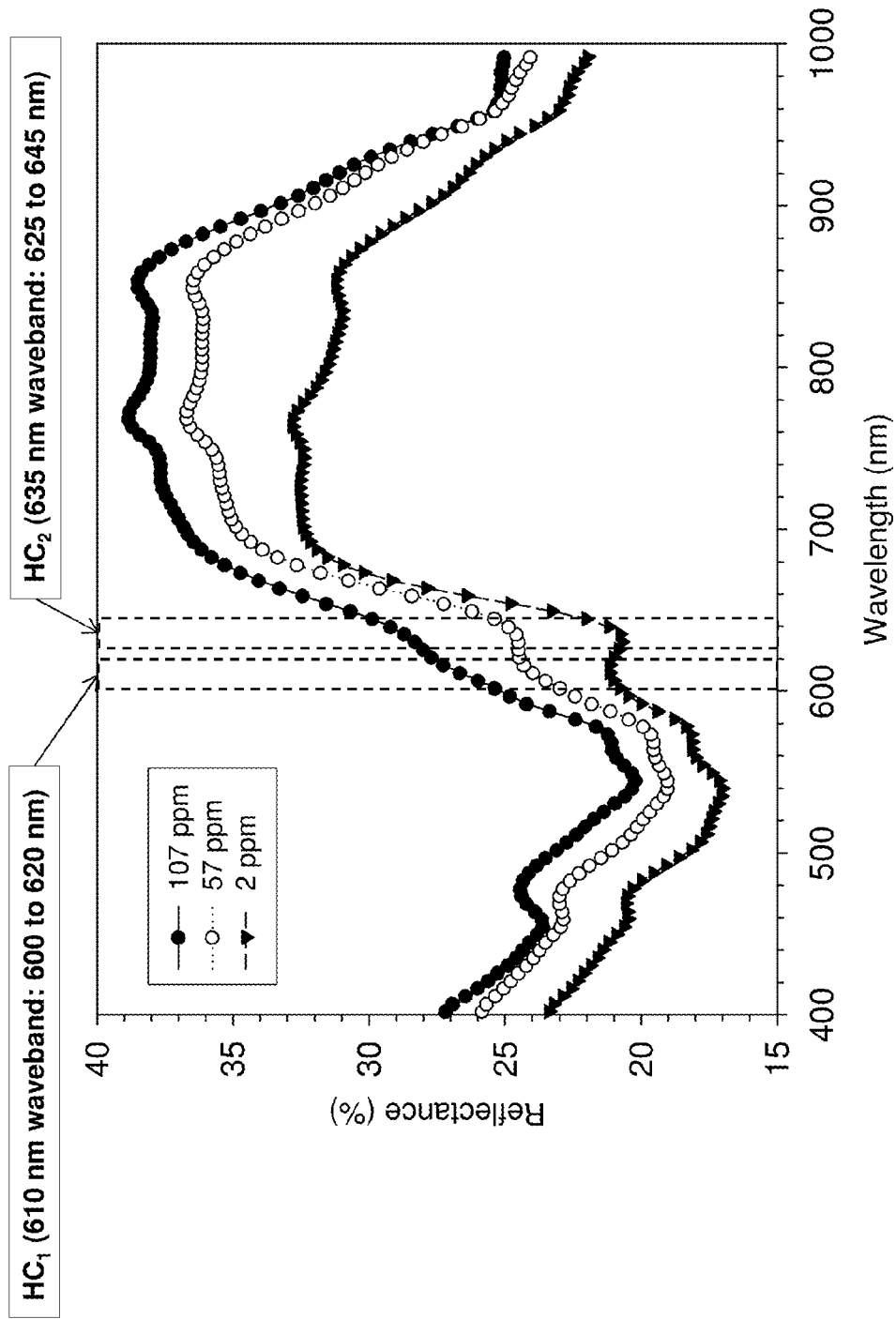
FIG. 3 is an exemplary hyperspectral scan of relative reflectance (%) versus light wave length (nm) for the tuna samples shown in FIG. 4.
Figure 4:
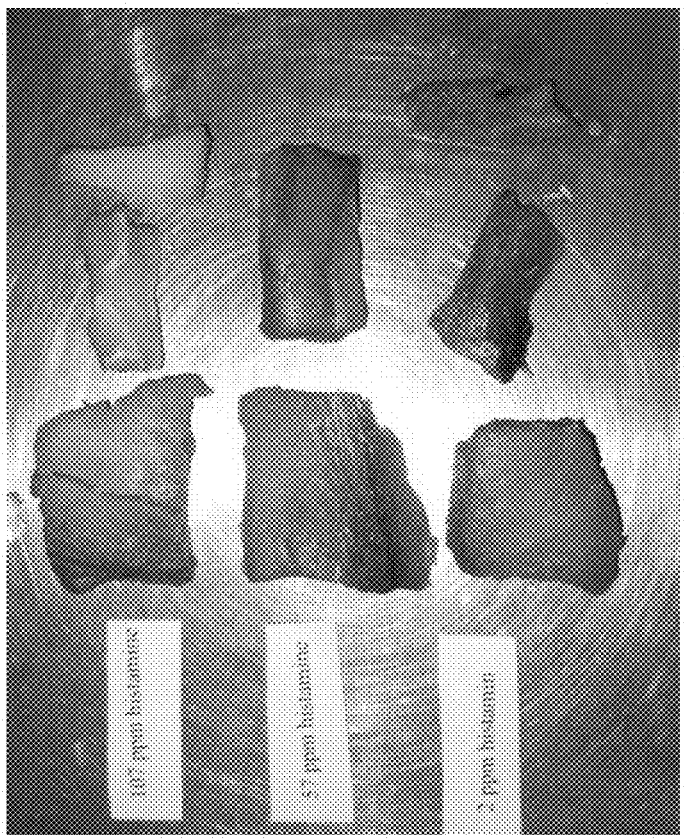
FIG. 4 is a photograph of tuna fish samples discussed in the Example section of this disclosure.

FIG. 3 shows an exemplary hyperspectral scan of relative reflectance (%) versus light wavelength (nm) for the tuna samples shown in FIG. 4. The key wavebands ($HC_1$=610 nm±10 nm, and $HC_2$=635 nm±10 nm) are clearly shown in FIG. 3.

The ratio of reflectance intensities $HC_2/HC_1$, is designated as HCR. An HCR value is determined for every fish pixel of the line scan image data. The inventors have found that the HCR value correlates with histamine concentration. The HCR values for each fish pixel are compared to an empirical (or, alternatively, a mathematically or biologically derived) database to determine a histamine concentration value for each fish pixel. A wholesome/unwholesome determination can be made based on the collective histamine concentration values for the fish pixels.

Once the histamine concentration values for each pixel of the fish image is determined, a histamine concentration image is produced by shading each of the original fish pixels based on the level of histamine concentration. A wholesome/unwholesome determination may be made based on the histamine concentration image.

Figure 6:
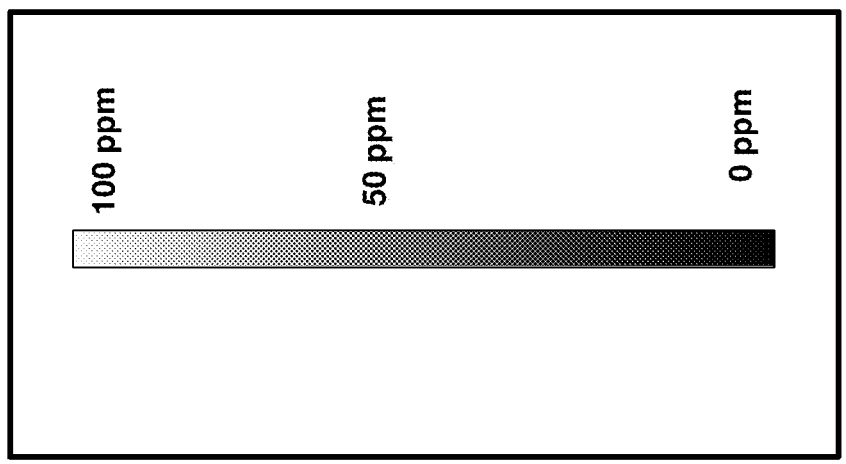
FIG. 6 is a visual scale showing the grayscale spectrum of histamine contamination for the image shown in FIG. 5.
Figure 5:
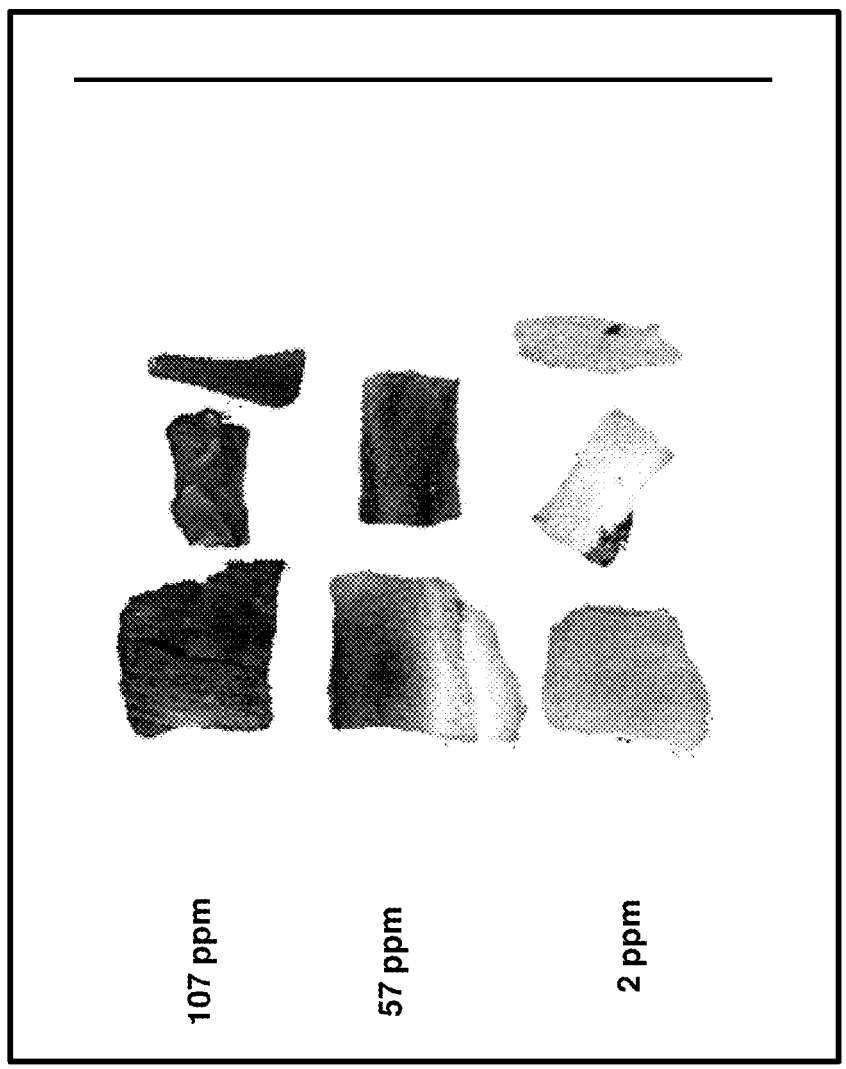
FIG. 5 is a grayscale histamine concentration image of the fish samples shown in FIG. 4.
Figure 8:
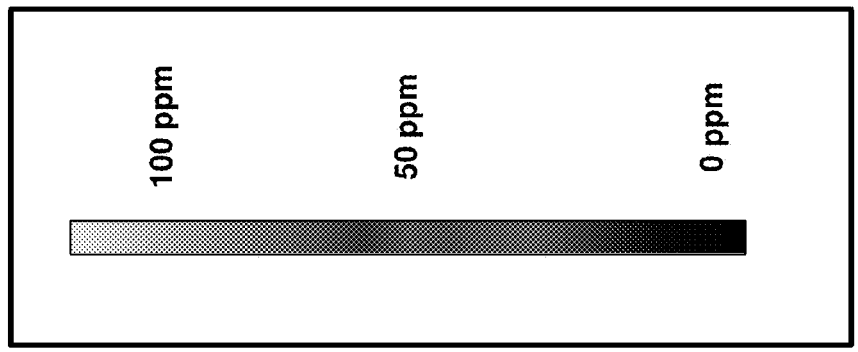
FIG. 8 is a visual scale showing the color spectrum of histamine contamination for the image shown in FIG. 7.

FIG. 6 shows the pixel intensity spectrum in grayscale, and FIG. 8 shows the pixel intensity spectrum in a color. As a general rule, higher concentrations of histamine are indicated by lighter and brighter colors, so that in visual inspections of the histamine concentration image, lighter and brighter colors alert an operator to high histamine concentration levels. Alternatively, the spectrum may be reversed. Histamine concentration images generated in grayscale and in color are shown in FIG. 5 (grayscale) and FIG. 7 (color), respectively.

If a portion of the fish exceeds the operator's "acceptable" histamine concentration threshold, then the fish is removed from the inspection process and further processed according to the operator's specific histamine contamination mitigation policy. At the operator's option, the entire affected fillet may be discarded. Alternatively, an operator may elect to review histamine concentration images (such as those shown in FIG. 5 and/or FIG. 7) and remove only those areas of the fillet which exceed the acceptable histamine concentration threshold. By removing only the unwholesome portions of the fish, an operator minimizes waste while still delivering fish items that meet or exceed the operator's and buyer's standards.

Figure 2:
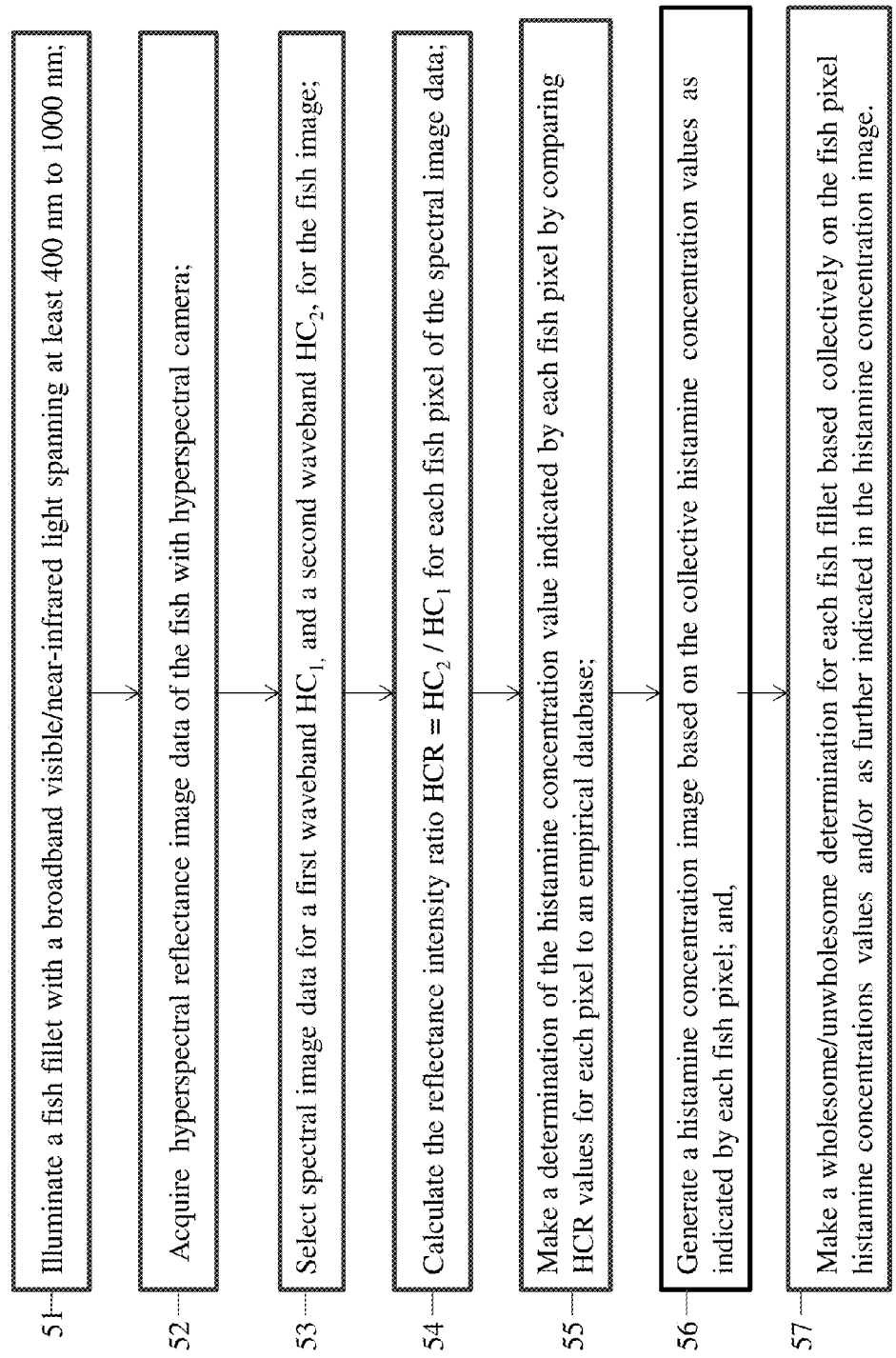
FIG. 2 is a flow diagram describing primary steps of the current method.

FIG. 2 comprises a flowchart-type diagram that summarizes the primary steps (numbered 51-57) of the method described herein. In the preferred embodiment, the steps associated with FIG. 2 reference numbers 53-57 are done autonomously, as directed by computer processor software.

In operation, in the preferred embodiment, a fish item 14 is illuminated by a broad spectrum light (at least 400-1000 nm) 12. A line scan image camera 20 with an imaging spectragraph 21 acquires a hyperspectral reflectance image of the fish 14. Spectral image data for a first ($HC_1$) and a second ($HC_2$) waveband is selected and a ratio (HCR) of the first waveband to the second waveband is calculated (i.e. HCR=$HC_2/HC_1$). An HCR value is calculated for each fish pixel of the spectral image.

A histamine concentration value is determined by comparing the calculated HCR values with an empirical data base correlating HCR values with histamine contamination levels. A color and/or grayscale image is generated based on the histamine contamination level associated with each fish pixel. The histamine contamination image may be displayed on a computer monitor associated with the computer station 40. If a portion of the fish exceeds the operator's histamine concentration threshold, then the fish is removed from the inspection process and further processed according to the operator's specific histamine contamination mitigation policy.

At the operator's option, a histamine concentration image (such as FIG. 5 or 7) may be used as a guide to identify and surgically remove an unwholesome portion(s) of the fish. The process described herein may be automated so that fish exceeding a maximum allowable histamine level are automatically removed.

EXAMPLE

A sampling of tuna fillets was collected from a conventional tuna processing line. A photograph of the tuna fillets displayed in conventional lighting on a stainless steel background is shown in FIG. 4. As indicated by the labels shown in the FIG. 4 photo, the fillets in the top row have a previously determined histamine concentration level of about 107 ppm. The fillets in the middle row have a histamine concentration level of about 57 ppm. The fillets on the bottom row have a histamine concentration level of about 2 ppm. FIG. 3 shows hyperspectral reflectance spectra of the tuna fillets shown in FIG. 4.

Figure 7:
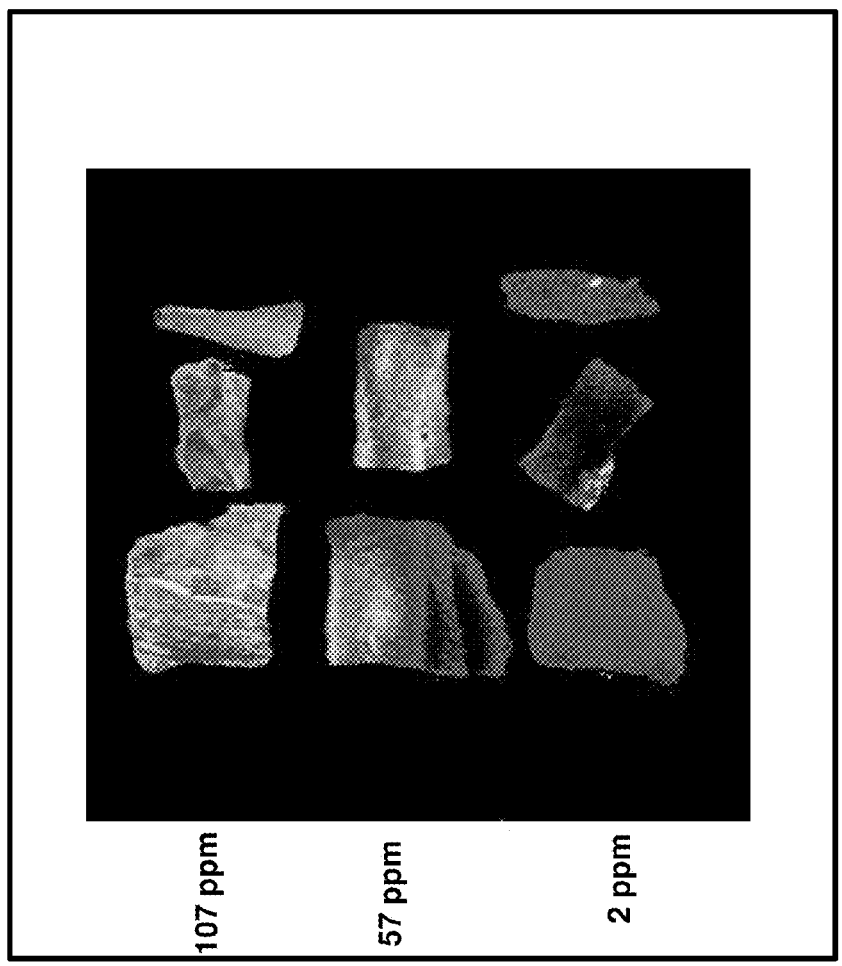
FIG. 7 is a color histamine concentration image of the fish samples shown in FIG. 4.

As described in FIG. 2, the hyperspectral image data was processed and $HC_1$, $HC_2$, and HCR were calculated, and a histamine concentration value was determined for each fish pixel in the hyperspectral fish image. FIG. 5 shows the resulting grayscale histamine concentration image, and FIG. 7 shows the resulting color histamine concentration image.

For the foregoing reasons, it is clear that the method described herein provides an innovative spectral method for determining the histamine concentration in fish. The current method may be modified in multiple ways and applied in various technological applications. The disclosed method may be modified and customized as required by a specific operation or application, and the individual components may be modified and defined, as required, to achieve the desired result.

Although the materials of construction are not described, they may include a variety of compositions consistent with the function described herein. Such variations are not to be regarded as a departure from the spirit and scope of this disclosure, and all such modifications as would be obvious to one skilled in the art are intended to be included within the scope of the following claims.

What is claimed is:

1. A method of distinguishing wholesome fish from unwholesome fish, the method comprising:
    (a) illuminating a fish item;
    (b) acquiring a hyperspectral reflectance fish image data,
    (c) within the hyperspectral fish image, selecting reflectance intensity data associated with a first light waveband (designated HC1), and a second light waveband (designated HC2), wherein the HC1 and HC2 are selected from the hyperspectral fish image; and, (d) applying an algorithm comprising HC1 and HC2 to the hyperspectral fish image to distinguish wholesome fish from unwholesome fish;

wherein, in step (d), the algorithm comprises:

(e) calculating a reflectance intensity ratio (designated HCR) for each fish pixel within the hyperspectral fish image, so that HCR=HC2/HC1;

(f) comparing HCR values for each fish pixel to a database and thereby determining a histamine concentration value indicated by each fish pixel; and, (g) distinguishing wholesome fish from unwholesome fish based on the collective histamine concentration values derived in step (f).

2. The method of claim 1 wherein, in step (d) the algorithm determines a histamine concentration in the fish.

3. The method of claim 1 wherein, in step (f), the histamine concentration value indicated by each fish pixel is used to generate a histamine concentration image, and the histamine concentration image is used to distinguish wholesome fish from unwholesome fish.

4. The method of claim 1 wherein, in step (a), the fish is illuminated with a spectrum of light that includes at least 400 nm-1000 nm.

5. The method of claim 1 wherein, in step (b), the hyperspectral fish image is a line scan image.

6. The method of claim 5, wherein the hyperspectral fish image is acquired by a camera system comprising an imaging spectrograph.

7. The method of claim 1 wherein, in step (c), HC1 is 610 nm±10 nm, and HC2 is 635 nm±10 nm.

8. The method of claim 1 wherein, in step (f), the data base is an empirical data base.

9. The method of claim 1 wherein, in step (f), the data base is a non-empirical data base.

10. The method of claim 3 wherein the histamine concentration image is displayed on a monitor, or the image is printed.

11. The method of claim 10 wherein the histamine concentration image is used to guide an operator to identify and remove a portion of the fish which exceeds an acceptable histamine concentration level.

12. The method of claim 3 wherein the histamine concentration image comprises a color image.

13. The method of claim 12 wherein areas of high histamine concentrations are shown as light and bright colors in the histamine concentration image.

14. The method of claim 3 wherein the histamine concentration image comprises a grayscale image.

15. The method of claim 14 wherein areas of high histamine concentrations are shown as light and near-white grayscale in the histamine concentration image.

16. The method of claim 1 wherein a computer processor automatically executes steps (b)-(d) and produces a histamine concentration image.

17. The method of claim 16 wherein the fish item is positioned on a conveyor and the processor directs that the fish item is automatically removed from the conveyor if the fish is unwholesome.

18. The method of claim 1 wherein, in step (a), the fish comprises a member of the Scrombroidae family.

19. The method of claim 1 wherein, in step (a), the fish comprises tuna, mahi mahi, or bluefish.

\* \* \* \* \*